United States Patent
Shah et al.

(10) Patent No.: US 10,729,685 B2
(45) Date of Patent: Aug. 4, 2020

(54) ORALLY ADMINISTRABLE COMPOSITIONS AND METHODS OF DETERRING ABUSE BY INTRANASAL ADMINISTRATION

(71) Applicant: Inspirion Delivery Sciences, LLC, Morristown, NJ (US)

(72) Inventors: Manish S. Shah, West Caldwell, NJ (US); Ray J. DiFalco, Ridgewood, NJ (US); Stefan Aigner, Valley Cottage, NY (US)

(73) Assignee: OHEMO Life Sciences Inc., Juncos, PR (US)

( * ) Notice: Subject to any disclaimer, the term of this patent is extended or adjusted under 35 U.S.C. 154(b) by 0 days.

(21) Appl. No.: 14/486,433

(22) Filed: Sep. 15, 2014

(65) Prior Publication Data

US 2016/0074383 A1 Mar. 17, 2016

(51) Int. Cl.
| | |
|---|---|
| *A61K 9/20* | (2006.01) |
| *A61K 9/26* | (2006.01) |
| *A61K 31/44* | (2006.01) |
| *A61K 31/485* | (2006.01) |
| *A61K 9/14* | (2006.01) |
| *A61K 9/00* | (2006.01) |
| *A61K 31/4468* | (2006.01) |

(52) U.S. Cl.
CPC .......... *A61K 31/485* (2013.01); *A61K 9/0043* (2013.01); *A61K 9/145* (2013.01); *A61K 9/146* (2013.01); *A61K 9/2018* (2013.01); *A61K 9/2054* (2013.01); *A61K 31/4468* (2013.01)

(58) Field of Classification Search
CPC ... A61K 9/2018; A61K 9/2054; A61K 31/485
USPC .................. 424/465, 468; 514/282
See application file for complete search history.

(56) References Cited

U.S. PATENT DOCUMENTS

| | | | |
|---|---|---|---|
| 3,980,766 A | 9/1976 | Shaw et al. | |
| 4,070,494 A | 1/1978 | Hoffmeister et al. | |
| 4,361,546 A | 11/1982 | Stricker et al. | |
| 4,423,099 A | 12/1983 | Mueller et al. | |
| 4,459,279 A | 7/1984 | Stricker et al. | |
| 4,784,858 A | 11/1988 | Ventouras | |
| 4,865,849 A | 9/1989 | Conte et al. | |
| 4,996,047 A | 2/1991 | Kelleher et al. | |
| 5,068,112 A | 11/1991 | Samejima et al. | |
| 5,206,030 A | 4/1993 | Wheatley et al. | |
| 5,395,626 A | 3/1995 | Kotwal et al. | |
| 5,474,786 A | 12/1995 | Kotwal et al. | |
| 5,484,608 A | 1/1996 | Rudnic et al. | |
| 5,614,218 A | 3/1997 | Olsson et al. | |
| 5,639,476 A | 6/1997 | Oshlack et al. | |
| 5,645,858 A | 7/1997 | Kotwal et al. | |
| 5,866,161 A | 2/1999 | Childers et al. | |
| 5,955,104 A | 9/1999 | Momberger et al. | |
| 5,958,459 A | 9/1999 | Chasin et al. | |
| 6,066,339 A | 5/2000 | Stark et al. | |
| 6,159,501 A * | 12/2000 | Skinhoj ................ | A61K 9/5084 424/451 |
| 6,277,384 B1 | 8/2001 | Kaiko et al. | |
| 6,309,668 B1 | 10/2001 | Bastin et al. | |
| 6,310,072 B1 | 10/2001 | Smith et al. | |
| 6,375,957 B1 | 4/2002 | Kaiko et al. | |
| 6,419,954 B1 | 7/2002 | Chu et al. | |
| 6,475,494 B2 | 11/2002 | Kaiko et al. | |
| 6,531,152 B1 | 3/2003 | Lerner et al. | |
| 6,720,005 B1 | 4/2004 | Ayres | |
| 6,753,011 B2 | 6/2004 | Faour | |
| 6,911,217 B1 | 6/2005 | Gren et al. | |
| 6,929,803 B2 | 8/2005 | Wong et al. | |
| 7,316,821 B2 | 1/2008 | Oshlack et al. | |
| 7,955,619 B2 | 6/2011 | Shah et al. | |
| 2003/0068371 A1 | 4/2003 | Oshlack et al. | |
| 2003/0068375 A1 | 4/2003 | Wright et al. | |
| 2003/0092724 A1 | 5/2003 | Kao et al. | |
| 2003/0099711 A1 | 5/2003 | Meadows et al. | |
| 2003/0118641 A1 | 6/2003 | Maloney et al. | |
| 2003/0157167 A1 | 8/2003 | Kao et al. | |
| 2003/0180359 A1 | 9/2003 | Vergnault et al. | |
| 2003/0180362 A1 | 9/2003 | Park et al. | |
| 2003/0198674 A1 | 10/2003 | Curatolo et al. | |
| 2004/0052731 A1 | 3/2004 | Hirsh et al. | |
| 2004/0092542 A1 | 5/2004 | Oshlack et al. | |
| 2004/0122104 A1* | 6/2004 | Hirsh .................. | A61K 9/2054 514/620 |
| 2004/0131552 A1 | 7/2004 | Boehm | |
| 2004/0161382 A1 | 8/2004 | Yum et al. | |

(Continued)

FOREIGN PATENT DOCUMENTS

| | | |
|---|---|---|
| CA | 2 554 697 A1 | 4/2007 |
| DE | 102006051020 A1 | 4/2008 |

(Continued)

OTHER PUBLICATIONS

"Avinza (morphine sulfate) Capsule, Extended Release [Ligand Pharmaceuticals Inc.]", DailyMed; Retrieved from http://www.dailymed.nlm.nih.gov/dailymed/druginfo.cfm?id=1435 (Jan. 2013).
"Eudragit RS PO—Eudragit—Targeted Drug Release and Tailored Service", Evonik Industries; retrieved from http://eudragit.evonik.com/product/eudragit/en/products-services/eudragit-products/sustained-release-form (2013).
Guidance for Industry: Dissolution Testing of Immediate Release Solid Oral Dosage Forms, U.S. Department of Health and Human Services, Federal Drug Administration, Center for Drug Evaluation and Research, Rockville, MD (2012).
"Opadry Complete Film Coating System", Colorcon; retrieved from http://www.colorcom.com/products/coatings/immediate-release/Opadry(2013).

(Continued)

*Primary Examiner* — Shengjun Wang
(74) *Attorney, Agent, or Firm* — Arent Fox LLP

(57) ABSTRACT

Orally administrable pharmaceutical compositions and methods of administration are provided. The pharmaceutical compositions provide abuse deterrent properties.

5 Claims, No Drawings

(56) References Cited

U.S. PATENT DOCUMENTS

| | | |
|---|---|---|
| 2004/0213849 A1 | 10/2004 | Sowden et al. |
| 2004/0228802 A1 | 11/2004 | Chang et al. |
| 2004/0253310 A1* | 12/2004 | Fischer ............... A61K 9/0092 424/472 |
| 2005/0020613 A1 | 1/2005 | Boehm et al. |
| 2005/0038121 A1 | 2/2005 | Mickle et al. |
| 2005/0074493 A1 | 4/2005 | Mehta et al. |
| 2005/0080012 A1 | 4/2005 | Mickle et al. |
| 2005/0112067 A1 | 5/2005 | Kumar et al. |
| 2005/0163843 A1 | 7/2005 | Boehm et al. |
| 2005/0176646 A1 | 8/2005 | Mickle et al. |
| 2005/0191349 A1 | 9/2005 | Boehm et al. |
| 2005/0214223 A1 | 9/2005 | Bartholomaeus et al. |
| 2005/0220715 A1 | 10/2005 | Lin |
| 2005/0245483 A1 | 11/2005 | Brogmann et al. |
| 2005/0266072 A1 | 12/2005 | Oshlack et al. |
| 2005/0266080 A1 | 12/2005 | Desai et al. |
| 2005/0281748 A1 | 12/2005 | Hirsh et al. |
| 2006/0014697 A1 | 1/2006 | Mickle et al. |
| 2006/0104909 A1 | 5/2006 | Vaghefi et al. |
| 2006/0110327 A1 | 5/2006 | Emigh et al. |
| 2006/0165602 A1 | 7/2006 | Galer et al. |
| 2006/0189635 A1 | 8/2006 | Kramer et al. |
| 2006/0251721 A1 | 11/2006 | Cruz et al. |
| 2007/0004797 A1 | 1/2007 | Weyers et al. |
| 2007/0020339 A1 | 1/2007 | Bear |
| 2007/0066537 A1 | 3/2007 | Mickle et al. |
| 2007/0128269 A1 | 6/2007 | Gervais et al. |
| 2007/0148097 A1 | 6/2007 | Finn et al. |
| 2007/0212414 A1 | 9/2007 | Baichwal et al. |
| 2007/0215511 A1 | 9/2007 | Mehta et al. |
| 2007/0259045 A1 | 11/2007 | Mannion et al. |
| 2007/0269505 A1 | 11/2007 | Flath et al. |
| 2008/0057123 A1 | 3/2008 | Grenier et al. |
| 2008/0069871 A1 | 3/2008 | Vaughn et al. |
| 2008/0069891 A1 | 3/2008 | Habib et al. |
| 2008/0085305 A1 | 4/2008 | Baichwal et al. |
| 2008/0260819 A1 | 10/2008 | Fleming et al. |
| 2008/0311205 A1 | 12/2008 | Habib et al. |
| 2009/0022794 A1 | 1/2009 | Johannson |
| 2009/0022798 A1 | 1/2009 | Rosenberg et al. |
| 2009/0081290 A1 | 3/2009 | McKenna et al. |
| 2009/0082466 A1 | 3/2009 | Babul |
| 2009/0232887 A1 | 9/2009 | Odidi et al. |
| 2009/0297617 A1 | 12/2009 | Rariy et al. |
| 2010/0015223 A1 | 1/2010 | Cailly-Dufestel et al. |
| 2010/0099696 A1 | 4/2010 | Soscia et al. |
| 2010/0112052 A1 | 5/2010 | Chen et al. |
| 2010/0221324 A1 | 9/2010 | Petereit et al. |
| 2010/0226978 A1 | 9/2010 | Petereit et al. |
| 2010/0239667 A1* | 9/2010 | Hemmingsen ....... A61K 9/2072 424/466 |
| 2011/0184007 A1 | 7/2011 | Shah et al. |
| 2012/0003311 A9 | 1/2012 | Yoshitake et al. |
| 2012/0202839 A1 | 8/2012 | Emigh et al. |

FOREIGN PATENT DOCUMENTS

| | | |
|---|---|---|
| EP | 0 092 060 A1 | 10/1983 |
| EP | 0682945 A2 | 11/1995 |
| FR | 2787715 A1 | 6/2000 |
| WO | WO 95/20947 A1 | 8/1995 |
| WO | WO 95/25506 A1 | 9/1995 |
| WO | WO 00/27364 A1 | 5/2000 |
| WO | WO 03/013479 A1 | 2/2003 |
| WO | WO 2004/037259 A1 | 5/2004 |
| WO | WO 2005/055981 A2 | 6/2005 |
| WO | WO 2005/117841 A1 | 12/2005 |
| WO | WO 2006/079550 A2 | 8/2006 |
| WO | WO 2006/089493 A1 | 8/2006 |
| WO | WO 2008/049657 A2 | 5/2008 |
| WO | WO 2009/092818 A1 | 7/2009 |

OTHER PUBLICATIONS

"Opana ER (oxymorphone hydrochloride) tablet, extended release [Endo Pharmaceuticals, Inc.]", DailyMed; retrieved from http://dailymed.nlm.nih.gov/dailymed/lookup.cfm?setid=545cea18-11ad-4881-b184-6f8bcc7908e4 accessed in Feb. 2013.

"Roxicodone—Oxycodone hydrochloride tablet", Xanodyne Pharmaceuticals, Inc.; retrieved from http://dailymed.nlm.nih.gov/dailymed/archives/fdaDrugInfo.cfm?archived=12847 on May 7, 2013.

"Substrate"—Chambers 21 st Century Dictionary, London: Chambers Harrap, 2001, Credo Reference.

Abbaspour et al., "Preparation and characterization of ibuprofen pellets based on Eudragit RS PO and RL PO or their combination," International Journal of Pharmaceutics, vol. 303, pp. 88-94 (2005).

Babak et al., "Impact of bulk and surface properties of some biocompatible hydrophobic polymers on the stability of methylene chloride-in-water mini-emulsions used to prepare nanoparticles by emulsification-solvent evaporation," Colloids and Surfaces B: Biointerfaces, vol. 59, pp. 194-207 (2007).

Chithaluru et al., "Formulation and Invitro Evaluation of Sustained Release Matrix Tablets of Losartan Potassium," Asian Journal of Pharmaceutical and Clinical Research, vol. 4, pp. 18-22 (2011).

Conte et al., "Multi-layered hydrophilic matrices as constant release devices (Geomatric™ Systems)," Journal of Controlled Release, vol. 26, pp. 39-47 (1993).

Conte et al., "Modulation of the dissolution profiles from Geomatrix® multi-layer matrix tablets containing drugs of different solubility," Biomaterials, vol. 17 No. 9, pp. 889-896 (1996).

Conte et al., "Press-coated tablets for time-programmed release of drugs," Biomaterials, vol. 14, No. 13, pp. 1017-1023 (1993).

Cozzolino et al., "Dye release behavior from polyvinyl alcohol films in a hydro-alcoholic medium: Influence of physicochemical heterogeneity," Colloids and Surfaces A: Physicochemical and Engineering Aspects, vol. 403, pp. 45-53 (2012).

Cremer, "Pharmaceutical Applications of Layer Tablets," Pharma Concepts GmbH & Co. KG (Berlin); vol. 249, pp. 1-4; retrieved from www.pharma-meggie.com (May 2001).

Efentakis et al., "Formulation study and evaluation of matrix and three-layer tablet sustained drug delivery systems based on Carbopols and isosorbite mononitrate," AAPS PharmSciTech, vol. 9, No. 3, pp. 917-923 (2008).

Fisher et al. "A Chronic Pain Management Manual," Writers Club Press, iUniverse Lincoln, NE; Appx. E. pp. 111-113 (2002).

Heng et al., "Mechanism of pellet coat rupture and its effect or drug release," Chem. Pharm. Bull., vol. 47, No. 7, pp. 939-943 (1999).

Kalantzi et al., "Recent advances in oral pulsatile drug delivery," Recent Patents on Drug Delivery and Formulation, vol. 3, pp. 49-63 (2009).

Kral et al. "Oxycodone Safety Handout for Patients," (2007) retrieved from www.Pain-Topics.org on May 7, 2013.

Murtaza, "Ethylcellulose Microparticles: A Reviews," Acta Poloniae Pharmaceutica—Drug Research, vol. 69, pp. 11-22 (2012).

Singh et al., "A diffusion controlled drug delivery system for theophylline," Drug Development and Industrial Pharmacy. vol. 20 No. 7, pp. 1225-1238 (1994).

Sutter et al., "Polymer films as diffusion barriers for oral controlled release preparation with special reference to aqueous dispersions," Acta Pharmaceutica Technologica, vol. 34, No. 4, pp. 179-188 (abstract) (1998).

Yang et al., "Accessibility of solid core tablet for dissolution in an asymmetric triple-layer matrix system," Journal of Pharmacy and Pharmacology, vol. 55, No. 1, pp. 1331-1337 (2003).

"Eudragit® NE 30D: Specification and Test Methods" Evonik Industries AG, Web, May 2014, http://www.eudragit.com. 5 pages.

"Oxycontin® (Oxycodone HCl Controlled-Release Tablets)" Monograph, Purdue Pharma, 2007, accessed at http://accessdata.fda.gov/drugsatfda_docs/label/2009/020553s060lbl.pdf. 32 pages.

Amabile et al. "Overview of Oral Modified-Release Opioid Products for the Management of Chronic Pain," Ann Pharmacother, 2006; 40:1327-1335.

Bajpai et al. "Responsive Polymers in Controlled Drug Delivery," Progress in Polymer Science 2008; 33:1088-1118.

Crowley et al. "Drug-Excipient Interactions," Pharmaceutical Technology, 2001, pp. 1-6.

(56) References Cited

OTHER PUBLICATIONS

Fujita et al, "Methodologies for regulation of intestinal absorption of biologically active peptides," Nippon Rinsho, Mar. 1998; 56(3): 589-594 (Abstract). 2 pages.
Gimbel et al. "The Efficacy and Safety of Oral Immediate-Release Oxymorphone for Postsurgical Pain," Anesth Analg, 2004; 99: 1472-1477.
Harris et al. "Abuse Potential, Pharmacokinetics, Pharmacodynamics, and Safety of Intranasally Administered Crushed Oxycodone HCI Abuse-Deterrent Controlled-Release Tablets in Recreational Opioid Users," The Journal of Clinical Pharmacology, 2013; 54(4):468-477.
Lenaerts et al. "Cross-linked high amylose starch for controlled release of drugs: recent advances," Journal of Controlled Release, 1998; 53: 225-234.
Meijerman et al. "Herb-Drug Interactions in Oncology: Focus on Mechanisms of Induction," The Oncologist, 2006; 11:742-752.
Overgaard et al. "Patient's evaluation of shape, size and colour of solid dosage forms," Pharm World Sci, 2001; 23(5): 185-188. 8 pages.
Page et al. "Innovations in oral gene delivery: challenges and potentials," DDT, 2001; 6(2): 92-101.
Savage et al. "Challenges in Using Opioids to Treat Pain in Persons with Substance Use Disorders," Addict. Sci. Clin. Pract., 2008; 4(2): 4-25.
Solinis et al. "Release in ketoprofen enantiomers from HPMC K100M matrices—diffusion studies," International Journal of Pharmaceutics, 2002; 239:61-68.
Van Zee, "The Promotion and Marketing of OxyContin: Commercial Triumph, Public Health Tragedy," American Journal of Public Health, 2009; 99:221-227.

\* cited by examiner

ORALLY ADMINISTRABLE COMPOSITIONS AND METHODS OF DETERRING ABUSE BY INTRANASAL ADMINISTRATION

FIELD OF THE INVENTION

The present invention provides orally administrable pharmaceutical compositions and methods of deterring abuse by intranasal administration.

BACKGROUND OF THE INVENTION

While pain medications, medications to reduce or eliminate anxiety attacks (psychotherapeutic drugs), stimulants and sleeping pills can be safe, effective, and therapeutically useful when administered properly, such drugs are susceptible to abuse. Examples of such compositions include but are not limited to ROXICODONE® (oxycodone tablets), OXYCONTIN® (oxycodone tablets), DILAUDID® (hydromorphone tablets), OPANA® and OPANA ER® (oxymorphone tablets), MS CONTIN® (morphine tablets), CONCERTA®, METHYLIN®, RITALIN®, RITALIN LA®, and EQUASYM KL® (methylphenidate tablets and capsules), FOCALIN® (dexmethylphenidate capsules), ADDERALL®, DEXEDRINE®, and DEXTROSTAT® (dextroamphetamine tablets and capsules), VYVANSE® (lisdexamfetamine capsules), ATIVAN® (lorazepam), XANAX® (alprazolam), and VALIUM® (diazepam).

A sense of euphoria or "high" can be experienced with high serum concentrations of these drugs. Individuals seeking to abuse these drugs will often tamper with oral dosage forms containing the drugs to achieve this "high." For example, a large amount of tablets can be placed in a liquid to form a solution, and abusers either consume the liquid or more often filter and inject the solution. These tablets can also be crushed into a powder or small particle sizes and snorted intranasally. Nasal insufflation, which is another term for the inhalation of substances through the nose, is a common and harmful practice among abusers. Long-term practice of nasal insufflation can result in permanent damage to nasal tissue and increased incidence of toxicity and overdose. There is a need in the art for pharmaceutical compositions which minimize the ability for abuse, and when administered properly, provide an adequate and effective amount of drug.

It is an object of the present invention to provide a pharmaceutical composition that reduces the potential for improper administration drugs but which, when administered as directed through oral administration, is capable of delivering a therapeutically effective dose to a subject. In particular, the present invention addresses the need for an orally administrable drug product which, compared to conventional formulations, decreases the ability of an individual to achieve a "high" or euphoria effect through injection or insufflation.

SUMMARY OF THE INVENTION

The present invention provides an orally administrable pharmaceutical composition comprising a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC of the drug achieved after a time period is lower than the Cmax and/or AUC of the drug achieved after intranasal administration of a physically compromised form of an orally bioequivalent composition not containing one or more pharmaceutically acceptable excipients in an amount sufficient to deter abuse by nasal insufflation.

The present invention also provides an orally administrable pharmaceutical composition comprising a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC achieved after a time period is no more than about 250% of the Cmax and/or AUC achieved after oral administration of the pharmaceutical composition in an intact form.

The present invention provides an orally administrable pharmaceutical composition of the present invention comprises a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC of a major metabolite of the drug achieved after intranasal administration after a time period is higher than the Cmax and/or AUC of the major metabolite of the drug achieved after intranasal administration of a physically compromised form of an orally bioequivalent composition not containing one or more pharmaceutically acceptable excipients in an amount sufficient to deter abuse by nasal insufflation after the same time period.

The present invention provides an orally administrable pharmaceutical composition of the present invention comprises a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the ratio of the AUC of the drug to the AUC of a major metabolite of the drug (drug:major metabolite) achieved after intranasal administration after a time period is lower than the ratio of the AUC of the drug to the AUC of a major metabolite of the drug (drug:major metabolite) achieved after intranasal administration of a physically compromised form of an orally bioequivalent composition not containing one or more pharmaceutically acceptable excipients in an amount sufficient to deter abuse by nasal insufflation after the same time period.

The present invention provides a method of treating, preventing, reducing the occurrence of, decreasing the severity or degree of, and/or reducing the signs and/or symptoms of a disease or condition in a subject in need thereof, wherein the disease or condition is selected from the group consisting of: pain, sleep disorders, anxiety, attention deficit hyperactivity disorder, narcolepsy, and depression in a subject in need thereof, comprising administering to the subject an orally administrable pharmaceutical composition comprising a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC of the drug achieved after a time period is lower than the Cmax and/or AUC of the drug achieved after intranasal administration of a physically compromised form of an orally bioequivalent composition not containing one or more pharmaceutically acceptable excipients in an amount sufficient to deter abuse by nasal insufflation.

The present invention provides a method of treating, preventing, reducing the occurrence of, decreasing the severity or degree of, and/or reducing the signs and/or symptoms of a disease or condition in a subject in need thereof, wherein the disease or condition is selected from the group consisting of: pain, sleep disorders, anxiety, attention deficit hyperactivity disorder, narcolepsy, and depression in a subject in need thereof, comprising administering to the subject an orally administrable pharmaceutical composition comprising a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC achieved after a time period is no more than about 250% of the Cmax and/or AUC achieved after oral administration of the pharmaceutical composition in an intact form.

The present invention provides a method of treating, preventing, reducing the occurrence of, decreasing the severity or degree of, and/or reducing the signs and/or symptoms of a disease or condition in a subject in need thereof, wherein the disease or condition is selected from the group consisting of: pain, sleep disorders, anxiety, attention deficit hyperactivity disorder, narcolepsy, and depression in a subject in need thereof, comprising administering to the subject an orally administrable pharmaceutical composition of the present invention comprises a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC of a major metabolite of the drug achieved after intranasal administration after a time period is higher than the Cmax and/or AUC of the major metabolite of the drug achieved after intranasal administration of a physically compromised form of an orally bioequivalent composition not containing one or more pharmaceutically acceptable excipients in an amount sufficient to deter abuse by nasal insufflation after the same time period The present invention provides a method of treating, preventing, reducing the occurrence of, decreasing the severity or degree of, and/or reducing the signs and/or symptoms of a disease or condition in a subject in need thereof, wherein the disease or condition is selected from the group consisting of: pain, sleep disorders, anxiety, attention deficit hyperactivity disorder, narcolepsy, and depression in a subject in need thereof, comprising administering to the subject an orally administrable pharmaceutical composition of the present invention comprises a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the ratio of the AUC of the drug to the AUC of a major metabolite of the drug (drug:major metabolite) achieved after intranasal administration after a time period is lower than the ratio of the AUC of the drug to the AUC of a major metabolite of the drug (drug:major metabolite) achieved after intranasal administration of a physically compromised form of an orally bioequivalent composition not containing one or more pharmaceutically acceptable excipients in an amount sufficient to deter abuse by nasal insufflation after the same time period

DETAILED DESCRIPTION OF THE INVENTION

In some embodiments, the orally administrable pharmaceutical composition of the present invention comprises a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC of the drug achieved after a time period is lower than the Cmax and/or AUC of the drug achieved after intranasal administration of a physically compromised form of an orally bioequivalent composition not containing one or more pharmaceutically acceptable excipients in an amount sufficient to deter abuse by nasal insufflation after the same time period. In preferred embodiments, the time period is selected from the group consisting of: 2 hours, 4 hours, 8 hours, 12 hours, and 24 hours. In some embodiments, the Cmax and/or AUC achieved after intranasal administration is at least 5% lower, alternatively at least 10% lower, alternatively at least 15% lower, alternatively at least 20% lower, alternatively at least 25% lower, alternatively at least 30% lower, alternatively at least 35% lower, alternatively at least 40% lower, alternatively at least 45% lower, alternatively at least 50% lower, alternatively at least 55% lower, or alternatively at least 60% lower than the Cmax and/or AUC achieved after intranasal administration of an orally bioequivalent composition after the same period of time.

The area under the curve, or "AUC" refers to the area under the serum concentration curve, or the integral of the blood serum concentration of the drug substance over a period of time. The term "Cmax" refers to the maximum or peak concentration observed after administration. The AUC and/or Cmax achieved after a period of time refers to the AUC and/or Cmax, respectively, calculated after a period of time after administration. In some embodiments, the period of time is about 30 minutes to about 24 hours after administration. In some embodiments, the period of time is selected from the group consisting of about 30 minutes, about 1 hour, about 2 hours, about 4 hours, about 8 hours, about 12 hours, and about 24 hours and the AUC and/or Cmax are calculated at any of these time points after administration. In some preferred embodiments, the period of time is selected from the group consisting of: about 0.5 hours, 1 hour, and 2 hours. In some embodiments, the AUC may refer to the "$AUC_{0\text{-}t}$". The term "$AUC_{0\text{-}t}$" refers to the AUC from time zero ("0") to "t" wherein "t" is the last time point with measurable concentration for individual formulation.

The present invention also provides an orally administrable pharmaceutical composition comprising a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC of the drug achieved after intranasal administration is no more than about 250% of the Cmax and/or AUC achieved after oral administration of the pharmaceutical composition in an intact form after the same period of time. In some embodiments, the Cmax and/or AUC is measured after a time period selected from the group consisting of: 2 hours, 4 hours, 8 hours, 12 hours, and 24 hours after administration. In some embodiments, the AUC refers to $AUC_{0-t}$. In some embodiments, the Cmax and/or AUC achieved after intranasal administration is no more than about 200%, alternatively no more than about 175%, alternatively no more than about 150% of the Cmax and/or AUC achieved after oral administration of the pharmaceutical composition in an intact form after the same period of time.

In some embodiments, the orally administrable pharmaceutical composition of the present invention comprises a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the Cmax and/or AUC of a major metabolite of the drug achieved after intranasal administration after a time period is higher than the Cmax and/or AUC of the major metabolite of the drug achieved after intranasal administration of a physically compromised form of an orally bioequivalent composition not containing one or more pharmaceutically acceptable excipients in an amount sufficient to deter abuse by nasal insufflation after the same time period. In preferred embodiments, the time period is selected from the group consisting of: 2 hours, 4 hours, 8 hours, 12 hours, and 24 hours. In some embodiments, the Cmax and/or AUC of a major metabolite of the drug after intranasal administration of the pharmaceutical composition of the present invention is at least 5% higher, alternatively at least 10% higher, alternatively at least 15% higher, alternatively at least 20% higher, alternatively at least 25% higher, alternatively at least 30% higher, than the Cmax and/or AUC of the major metabolite of the drug achieved after intranasal administration of an orally bioequivalent composition.

In some embodiments, the orally administrable pharmaceutical composition of the present invention comprises a drug and one or more pharmaceutically acceptable excipients in an amount sufficient to deter abuse by nasal insufflation, wherein the pharmaceutical composition is configured such that when the pharmaceutical composition is intranasally administered in physically compromised form to a subject, the ratio of the AUC of the drug to the AUC of a major metabolite of the drug (drug:major metabolite) achieved after intranasal administration after a time period is lower than the ratio of the AUC of the drug to the AUC of a major metabolite of the drug (drug:major metabolite) achieved after intranasal administration of a physically compromised form of an orally bioequivalent composition not containing one or more pharmaceutically acceptable excipients in an amount sufficient to deter abuse by nasal insufflation after the same time period. In preferred embodiments, the time period is selected from the group consisting of: 2 hours, 4 hours, 8 hours, 12 hours, and 24 hours. In some embodiments, the ratio (drug:major metabolite) after intranasal administration of the pharmaceutical composition of the present invention is at least 5% lower, alternatively at least 10% lower, alternatively at least 15% lower, alternatively at least 20% lower, than the ratio (drug:major metabolite) achieved after intranasal administration of an orally bioequivalent composition.

A "orally bioequivalent" drug composition refers to a pharmaceutical composition which contains the same drug(s) and which, when administered orally in intact form, has an AUC and/or Cmax within the range of 80 to 125% of the AUC and/or Cmax of the reference drug composition when administered orally in intact form. In some embodiments, the bioequivalent drug composition comprises the same drug and same amount of drug, but it may comprise different pharmaceutically acceptable excipients or a different amount of pharmaceutically acceptable excipients. In preferred embodiments, the orally bioequivalent drug composition does not contain one or pharmaceutically acceptable excipients in an amount sufficient to deter abuse by nasal insufflation.

The composition is "physically compromised" when it is in a form other than an intact form. This can be achieved by various means such as by chewing, chopping, grinding, crushing, or placing into solvents ex vivo, such as those containing an alcohol (e.g., ethyl alcohol) and/or water. In preferred embodiments, the physically compromised composition is in a chopped, ground, or crushed form. A pharmaceutical composition may be physically compromised in a number of ways, including but not limited to use of a pill crusher, a pill splitter, a mortar and pestle, a solid object such as a hammer or a spoon, a sharp object such as a razor, a grinder such as a coffee bean grinder, or a blender. In some embodiments, the average particle size of the physically compromised pharmaceutical composition is less than 6 mm, alternatively less than 5 mm, alternatively less than 4 mm, alternatively less than 3 mm, alternatively less than 2 mm, alternatively less than 1 mm, alternatively less than 0.5 mm, alternatively less than 0.25 mm.

The term "drug" includes any compound which has pharmacological or biological activity. A drug may comprise an active pharmaceutical ingredient or a salt, ester, or derivative thereof. In some embodiments, the drug can include, but is not limited to analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, neuroprotective agents, β-blockers, cardic inotropic agents, cell adhesion inhibitors, corticosteroids, cytokine receptor activity modulators, diuretics, anti-Parkinson's agents, gastro-intestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents; and salts, esters, and mixtures thereof. However, typically, the drug or drugs will be one that is often abused, such as central nervous system stimulants and depressants. Examples of central nervous system stimulants include, but are not limited amphetamines and agents such as cocaine. Examples of central nervous depressants include, but are not limited to opioids, barbiturates, benzodiazepines, and other anxiety and sleep medications. Examples of combinations of two drugs include oxycodone and morphine. In some embodiments, the composition may comprise an opioid and an opioid antagonist such as naltrexone.

Examples of opioids include, but are not limited to the following: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, nornormethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol. Any opioid or pharmaceutically acceptable salt or ester thereof may be used in the abuse deterrent composition. Preferred opioids include fentanyl, sufentanil, carfentanil, lofentanil, alfentanil, hydromorphone, oxycodone, morphine, hydroxycodone, propoxyphene, pentazocine, methadone, tilidine, butorphanol, buprenorphine, levorphanol, codeine, oxymorphone, meperidine, and dihydrocodeinone. More preferred opioids include oxycodone, hydrocodone, codeine, morphine, oxymorphone and hydromorphone, and pharmaceutically acceptable salts and esters thereof. The most particularly preferred opioids are oxycodone, oxymorphone, and morphine and pharmaceutically acceptable salts thereof.

A metabolite is a compound derived from the parent drug through Phase I and/or Phase II metabolic pathways. A major metabolite of a drug may refer to a metabolite which in the human plasma accounts for ≥10% of the parent drug systemic exposure or administered dose. The major metabolite may refer to active or inactive metabolites.

In some embodiments, the compositions of the present invention comprise morphine or a salt thereof. Morphine, also known as (5α,6α)-7,8-didehydro-4,5-epoxy-17-methylmorphinan-3,6-diol, is an example of a potent opioid analgesic used in the treatment of acute, chronic, and severe pain. Salts of morphine include, but are not limited to sulfate, sulfate pentahydrate, hydrochloride, hydrochloride trihydrate, meconate, valerate, acetate, citrate, bitartrate, stearate, phthalate, hydrobromide, hydroiodide, mucate, nitrate, salicylate, phenylpropionate, phosphate, methyliodide, isobutyrate, hypophosphite, tannate, tartrate, methylbromide, methylsulfonate, and those disclosed in EP 0137600, which is incorporated herein by reference. In preferred embodiments, the composition comprises morphine sulfate or morphine sulfate pentahydrate. Major metabolites of morphine include morphine-3-glucuronide (M3G), morphine-6-glucuronide (M6G), hydromorphone, normorphine (NM) and minor metabolites such as morphine-3,6-diglucuronide, morphine-3-ethereal sulfate, normorphine-6-glucuronide, and normorphine-3-glucuronide. Morphine-6-glucuronide (M6G), a major metabolite of morphine, is formed by glucuronidation. M6G and morphine both demonstrate analgesic activity.

In some embodiments, the compositions of the present invention comprise oxycodone or a salt thereof. Oxycodone, also known as (5R,9R,13S,14S)-4,5α-epoxy-14-hydroxy-3-methoxy-17-methylmorphinan-6-one, is an opioid analgesic used for the treatment of pain. Major metabolites of oxycodone include noroxycodone, α oxycodol, β oxycodol, oxymorphone, α oxymorphol, β oxymorphol, noroxymorphone, α noroxycodol, β noroxycodol, noroxymorphone, 14-hydroxydihydrocodeine, and 14-hydroxydihydromorphine. Oxymorphone and noroxycodone are the most commonly known major metabolites of oxycodone.

In some embodiments, the compositions of the present invention comprise oxymorphone or a salt thereof. Oxymorphone, also known as 14-hydroxydihydromorphinone and 4,5α-epoxy-3,14-dihydroxy-17-methylmorphinan-6-one, is an opioid analgesic used for the treatment of pain. Major metabolites of oxymorphone include oxymorphone-3-glucuronide and 6-hydroxy-oxymorphone.

In some embodiments, the compositions of the present invention comprise hydrocodone or a salt thereof. Hydrocodone, which is also known as 4,5a-epoxy-3-methoxy-17-methylmorphinan-6-one, is an opioid analgesic used for the treatment of pain. Major metabolites of hydrocodone include norhydrocodone and hydromorphone.

In some embodiments, the compositions of the present invention comprise hydromorphone or a salt thereof. Hydromorphone, which is also known as 4,5-α-epoxy-3-hydroxy-17-methyl morphinan-6-one, is an opioid analgesic. Major metabolites of hydromorphone include hydromorphone-3-glucuronide, hydromorphone-3-glucoside and dihydroisomorphine-6-glucuronide.

In some embodiments, the compositions of the present invention comprise codeine or a salt thereof. Codeine, which is also known as a (5α,6α)-7,8-didehydro-4,5-epoxy-3-methoxy-17-methylmorphinan-6-ol, is an opioid used for its analgesic, antitussive, antidiarrheal, antihypertensive, anxiolytic, antidepressant, sedative and hypnotic properties. Major metabolites of codeine include codeine-6-glucuronide (C6G), norcodeine, hydrocodone, morphine, morphine-3-glucuronide, morphine-6-glucuronide, and normorphine.

In some embodiments, the compositions of the present invention comprise a barbiturate or a salt thereof. Examples of barbiturates include, but are not limited to mephobarbital (which is sometimes marketed under the tradename MEBARAL®) and pentobarbital sodium (which is sometimes marketed under the tradename NEMBUTAL®). Barbiturates are often prescribed to treat anxiety, tension, and sleep disorders.

In some embodiments, the compositions of the present invention comprise a benzodiazepine or a salt or derivative thereof. Examples of benzodiazepines and benzodiazepine derivatives include, but are not limited to diazepam (sometimes marketed under the tradename VALIUM®), alprazolam (sometimes marketed under the tradename XANAX®), lorazepam (sometimes marketed under the tradename ATIVAN®, triazolam (sometimes marketed under the tradename HALCION®), and estazolam (sometimes marketed under the tradename PROSOM®). Benzodiazepines are often prescribed to treat anxiety, acute stress reactions, and panic attacks.

Alprazolam, which is also known as 8-chloro-1-methyl-6-phenyl-4H-[1,2,4]triazolo[4,3-a][1,4]benzodiazepine, is a short acting anxiolytic. Major metabolites of alprazolam include, but are not limited to 4-hydroxyalprazolam and α-hydroxyalprazolam.

Lorazepam, which is also known as (RS)-7-Chloro-5-(2-chlorophenyl)-3-hydroxy-1,3-dihydro-2H-1,4-benzodiazepin-2-one, is an anxiolytic agent having intermediate duration of action. Major metabolites of lorazepam include, but are not limited to, 3-O-phenolic glucuronide and lorazepam glucuronide.

Diazepam, which is also known as 7-chloro-1,3-dihydro-1-methyl-5-phenyl-1,4-benzodiazepin-2(3H)-one, is a commonly used anxiolytic. Major metabolites of diazepam include, but are not limited to desmethyldiazepam, esmethyldiazepam, oxazepam, and temazepam.

In some embodiments, the compositions comprise a CNS depressant such as zaleplon, which is sometimes marketed under the tradename SONATA®, and zolpidem, which is sometimes marketed under the tradename AMBIEN®.

In some embodiments, the compositions of the present invention comprise a central nervous stimulant or salt thereof. Central nervous stimulants are often used to increase mental alertness, and they can results in feelings of exhilaration and energy. Stimulants often increase heart rate, blood pressure and metabolism. Amphetamines such as methylphenidate (sometimes marketed under the tradename RITALIN®) and dextroamphetamine (sometimes marketed under the tradenames ADDERALL® and DEXEDRINE®) are often prescribed for the treatment of narcolepsy, attention-deficit/hyperactivity disorder, and depression that has not responded to other treatments. Examples of such central nervous stimulants include, but are not limited to, amphetamines such as methylphenidate, dextroamphetamine, and lisdexamfetamine.

Methylphenidate, which is also known as methyl phenyl (piperidin-2-yl)acetate, is a drug often used for treatment of narcolepsy, attention-deficit/hyperactivity disorder, and depression. Major metabolites of methylphenidate include but are not limited to ethylphenidate, ritalinic acid (α-phenyl-2-piperidine acetic acid), hydroxymethylphenidate, and hydroxyritalinic acid.

Dextroamphetamine, which is also known as (2S)-1-phenylpropan-2-amine, is a drug used for treatment of narcolepsy, attention-deficit/hyperactivity disorder, and depression. Major metabolites of dextroamphetamine include but are not limited to 4-hydroxyamphetamine, benzoic acid, phenylacetone, hippuric acid, 4-hydroxynorephedrine, and norephedrine.

Lisdexamfetamine, also known as lisdexamfetamine, is another stimulant. It is a prodrug of phenethylamine and amphetamines such as dextroamphetamine.

The present invention provides for compositions comprising one or more drugs. In some embodiments, the compositions comprise one or more opioids. The present invention also provides for compositions comprising one or more opioids, wherein the compositions do not comprise an opioid antagonist or any other drug that is not an opioid agonist. The present invention provides for compositions comprising one or more drugs but not comprising any adverse agent. Adverse agents refer to agents which reduce or eliminate one or more pharmacological effects of the drug or agents which cause an undesired physiological reaction, such as emesis. Adverse agents include, but are not limited to antagonists such as opioid antagonists, mucous membrane irritants, and emetics. The present invention provides compositions which do not comprise naloxone or naltrexone.

Preferred embodiments of the invention include a drug and amounts as follows: oxycodone or a pharmaceutically acceptable salt thereof, which is present in an amount of about 5 mg to about 400 mg; morphine or a pharmaceutically acceptable salt thereof, which is present in an amount of about 15 mg to about 800 mg; hydromorphone or a pharmaceutically acceptable salt thereof, which is present in an amount of about 1 mg to about 64 mg; hydrocodone or a pharmaceutically acceptable salt thereof, which is present in an amount of about 5 mg to about 400 mg; and oxymorphone or a pharmaceutically acceptable salt thereof, which is present in an amount of about 4 mg to about 80 mg.

The compositions of the present invention comprise one or more pharmaceutically acceptable excipients. Examples of pharmaceutically acceptable excipients include but are not limited to plasticizers, anti-adhesive, inert fillers, lipophilic agents and pigments used in a known manner. Examples of anti-adhesive are metallic stearates, microcrystalline cellulose, calcium phosphate, AEROSIL® 200, and talc. Examples of plasticizers for use in accordance with the present invention include triacetin, acetylated monoglyceride, olive oil, acetyl tributyl citrate, acetyl triethyl citrate, glycerin, sorbitol, polyethylene glycol, and polypropyleneglycol. Fillers/diluents/binders may be incorporated such as sucrose, sorbitol, mannitol, various grades of lactose, various grades of microcrystalline cellulose, dextrins, maltodextrins, starches or modified starches, sodium phosphate, calcium phosphate, calcium carbonate, gelatin, polyvinylpyrrolidone, and sodium carboxymethylcellulose. Disintegrants may be used such as cellulose derivatives, including microcrystalline cellulose, low-substituted hydroxypropyl cellulose, croscarmellose sodium, alginic acid, insoluble polyvinlypyrrolidone, and sodium carboxymethyl starch. Glidants and lubricants may be incorporated such as stearic acid, metallic stearates such as magnesium stearate, talc, waxes, and glycerides with high inciting temperatures, colloidal silica, sodium stearyl fumarate, polyethyleneglycols, and alkyl sulphates. Surfactants may be employed such as non-ionic (various grades of polysorbate); anionic such as docusate sodium and sodium lauryl sulfate, and cationic such as benzalkonium chloride. An example of an amphoteric surfactant is 1,2-diacyl-L-phosphatidylcholine. The preferred surfactants are TWEEN® 80, BRIJ®, and Nanoxyl-100. Other appropriate pharmaceutically acceptable excipients may include colorants, flavoring agents, pH adjusting agents, solubilizing agents, wetting agents, solvent resistant agents and buffering agents.

In some preferred embodiments, the composition comprises one or more of the following types of pharmaceutically acceptable excipients: disintegrants, filler/diluent/binders, glidants and lubricants. In some embodiments, the composition comprises a mixture of one or more pharmaceutically excipients. In some embodiments, the composition comprises a mixture of a sugar alcohol such as mannitol, a lubricant such as magnesium stearate, and microcrystalline cellulose.

In preferred embodiments, the compositions of the present invention comprise one or more pharmaceutically acceptable excipients in an amount sufficient to deter abuse by nasal insufflation. Nasal insufflation may be deterred in a number of ways, including but not limited to providing a high or euphoric effect which is substantially the same as or less than the euphoric effect achieved by oral administration of an intact dosage form and/or a physically compromised dosage form. Another way to deter abuse by nasal insufflation is by providing an undesirable or adverse effect, such as nasal irritation or damage to the nasal mucosa. Substantially the same means within 20% and preferably within 10%. Euphoria is a high or feeling of extreme elation, which is often experienced after an abuser is administered a pharmaceutical composition containing a central nervous system drug. The amount or intensity of euphoria, or the euphoric effect, can be measured in a number of different ways. Methods or techniques of measuring euphoria are sometimes similar to methods or techniques of measuring other conditions, such as pain. For example, the amount or intensity of euphoria can be measured in a numerical or linear scale, and the person experiencing the euphoria can quantify or rate the amount or intensity of the euphoria. For example, in some embodiments, the amount or intensity of euphoria can be measured on a scale from 0 to 10, wherein a high amount of euphoria is designated by the number 10, and no euphoria is designated by the number 0. Similarly, in some embodiments, the amount or intensity of euphoria can be measured on a linear scale, wherein one end of the line represents no euphoria, and the opposite end of the line represents a high amount of euphoria.

In some embodiments, the one or pharmaceutically acceptable excipients may be in an amount sufficient to deter abuse by nasal insufflation when the composition comprises an active ingredient and one or more pharmaceutically acceptable excipients, wherein the ratio of the amount of pharmaceutically acceptable excipients in the composition to the amount of pharmaceutically acceptable excipient in an orally bioequivalent composition is greater than 1:1. In some embodiments, the ratio is about 2:1 or greater, preferably about 2.5:1 of greater, more preferably about 3:1 or greater, more preferably about 3.5:1 or greater, and most preferably about 4:1 or greater. In some embodiments, the ratio is about 5:1 or greater.

In some embodiments, the one or pharmaceutically acceptable excipients may be in an amount sufficient to deter abuse by nasal insufflation when the composition comprises one or more pharmaceutically acceptable excipients in an amount of at least 40%, alternatively at least 45%, alternatively at least 50%, alternatively at least 55%, alternatively at least 60%, alternatively at least 65%, alternatively at least 70%, alternatively at least 75%, alternatively at least 80%, alternatively at least 85%, alternatively at least 90%, alternatively at least 95% by weight of the total weight of the composition. In some embodiments, the composition comprises one or more pharmaceutically acceptable excipients in an amount of about 75% or more, alternatively about 80% or more, alternatively about 85% or more, or alternatively about 90% or more by weight of the total weight of the composition. In some embodiments, the bioequivalent composition not configured to deter abuse comprises one or more pharmaceutically acceptable excipients in an amount less than the amount present in a composition of the present composition. In some embodiments, the orally bioequivalent composition, which in some embodiments is a bioequivalent composition not configured to deter abuse, comprises one or more pharmaceutically acceptable excipients in an amount of less than about 90%, alternatively about 85% or less, alternatively about 80% or less, alternatively about 75% or less, alternatively about 70% or less, alternatively about 65% or less, alternatively about 60% or less, by weight of the total weight of the composition.

In some embodiments, the one or pharmaceutically acceptable excipients may be in an amount sufficient to deter abuse by nasal insufflation when the composition comprises the active ingredient and the one or more pharmaceutically acceptable excipients in a ratio of pharmaceutically acceptable excipient:active ingredient of 1:1 or more, alternatively 2:1 or more, alternatively 3:1 or more, alternatively 4:1 or more, or alternatively 5:1 or more.

The pharmaceutical composition may be formulated for immediate release and/or extended release characteristics. The term "extended release" is used to refer to a composition which is formulated to provide for the gradual release of an active ingredient over an extended period of time, preferably over 2 to 48 hours, more preferably over 4 to 36 hours, and most preferably over 6 to 24 hours. The term "extended release" includes controlled release and delayed release. In some embodiments of the present invention containing an extended release portion, preferably <25%, more preferably <20%, of the active ingredient is released in the first hour from the extended release portion; preferably 15-50%, more preferably 20-45%, of the active ingredient is released in the first two (2) hours from the extended release portion; preferably 40-80%, more preferably 45-75%, of the active ingredient is released in the first four (4) hours from the extended release portion; and preferably >75%, more preferably >80%, of the active ingredient is released after eight (8) hours from the extended release portion. In preferred embodiments, the pharmaceutical composition is formulated for immediate release. The term "immediate release" is used to refer to a pharmaceutical composition which is formulated to release about 80% or more of an active ingredient after 4 hours, more preferably after 2 hours, and most preferably after 1 hour after oral administration. In preferred embodiments, the pharmaceutical composition is formulated to release about 80% or more, more preferably about 90% or more, even more preferably about 95% of the active ingredient in the pharmaceutical composition after about 1 hour after oral administration of the unit dosage form (for example, after swallowing the tablet or capsule or other dosage form).

The pharmaceutical composition can be in any pharmaceutical dosage form, including, but not limited to a tablet, a capsule, a micro tablet, granules, pellets, a lollipop, a lozenge and a coated capsule. In preferred embodiments, the pharmaceutical composition comprises a tablet dosage form.

The present invention also provides methods of administering compositions of the present invention. The present invention provides a method of treating, preventing, reducing the occurrence of, decreasing the severity or degree of, and/or reducing the signs and/or symptoms of a disease or condition in a subject in need thereof, comprising administering to the subject a composition of the present invention. The disease or condition includes any disease or condition which would benefit from administration of a drug, including but not limited to analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, neuroprotective agents, β-blockers, cardic inotropic agents, cell adhesion inhibitors, corticosteroids, cytokine receptor activity modulators, diuretics, anti-Parkinson's agents, gastro-intestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents; and salts, esters, and mixtures thereof. In some embodiments, the disease or conditions is selected from the group consisting of: pain, sleep disorders (such as insomnia), anxiety, attention deficit hyperactivity disorder, narcolepsy, and depression. In some embodiments, the disease or condition includes, but not limited to, pain, chronic pain; acute pain; and/or pain associated with, secondary to, or caused by conditions such as osteoarthritis, rheumatoid arthritis, fibromyalgia, migraines and other headaches, back-related disorders, shingles, stiffened joints, physical trauma, cardiovascular conditions, cancer, sciatica, kidney stones, appendicitis, neuralgia, pancreatitis, gout, endometriosis, stomach ulcers, Crohn's Disease, and post-operative conditions.

In some embodiments, the compositions of the prevent invention may be administered at a frequency of one or more times every day. In some embodiments, the composition is administered one, two, or three times daily.

EXAMPLES

Example 1

The following study was conducted to test a Formulation containing 60 mg morphine sulfate pentahydrate and about 500 mg of pharmaceutically acceptable excipients. The pharmaceutically acceptable excipients comprise about 400 mg of a mixture of mannitol, AVICEL® PH 102 (microcrystalline cellulose) and magnesium stearate. The study was a randomized, double-blind study of 26 human subjects. The Formulation was crushed, and the following mean exposures ($AUC_{0-t}$) were observed.

|  | AUC (ng · h/mL) |
|---|---|
| Morphine | 165 |
| M6G | 761 |
| MOR/M6G | 0.22 |

Example 2

The following study compares the bioavailability and abuse potential of the Formulation of Example 1 and a Comparative Formulation (bioequivalent composition) containing morphine sulfate pentahydrate. The Formulation of Example 1 contains 60 mg of morphine sulfate pentahydrate and about 500 mg of pharmaceutically acceptable excipients. The Comparative Formulation contains 60 mg of morphine sulfate pentahydrate and about 100 mg of pharmaceutically acceptable excipients. The study is a randomized, double-blind study of human subjects. The Formulation of Example 1 and the Comparative Formulation are crushed. After intranasal administration, the following mean exposures ($AUC_{0-t}$) are observed. The Comparative Formulation, which contains less excipient, results in higher levels of morphine (MOR), lower levels of morphine 6-glucuronide (M6G), and a high ratio of MOR:M6G (compared to the Formulation of Example 1). The Formulation of Example 1, which contains more excipient, displays low levels of morphine, high levels of M6G, and a low ratio of MOR/M6G.

What is claimed:

1. An orally administrable, extended release pharmaceutical composition in a single tablet unit dosage form configured to deter abuse by nasal insufflation, wherein the tablet unit dosage form comprises:

a drug comprising morphine or a salt thereof in an amount of about 60 mg, and about 500 mg of pharmaceutically acceptable excipients, wherein the tablet unit dosage form comprises about 400 mg of a mixture of magnesium stearate, microcrystalline cellulose, and mannitol, wherein when the pharmaceutical composition is intranasally administered in crushed form to a subject, the AUC of the drug achieved after a time period is lower than the AUC of the drug achieved after intranasal administration of a crushed form of an orally bioequivalent composition not containing about 400 mg of a mixture of magnesium stearate, microcrystalline cellulose, and mannitol, and wherein morphine or a salt thereof is the only active ingredient in the pharmaceutical composition.

2. The pharmaceutical composition of claim 1, wherein when the pharmaceutical composition is intranasally administered in crushed form to a subject, the AUC of the drug achieved after intranasal administration after a time period is at least 5% lower than the AUC of the drug achieved after intranasal administration of an orally bioequivalent composition in crushed form.

3. The pharmaceutical composition of claim 1, wherein when the pharmaceutical composition is intranasally administered in crushed form to a subject, the AUC of the drug achieved after intranasal administration after a time period is at least 10% lower than the AUC of the drug achieved after intranasal administration of an orally bioequivalent composition in crushed form.

4. The pharmaceutical composition of claim 1, wherein when the pharmaceutical composition is intranasally administered in crushed form to a subject, the AUC of the drug achieved after intranasal administration after a time period is at least 15% lower than the AUC of the drug achieved after intranasal administration of an orally bioequivalent composition in crushed form.

5. The pharmaceutical composition of claim 1, wherein the time period is selected from the group consisting of: 30 minutes, 1 hour, 2 hours, 4 hours, 8 hours, 12 hours, and 24 hours.

* * * * *